United States Patent
Marhold et al.

(10) Patent No.: US 7,148,384 B2
(45) Date of Patent: Dec. 12, 2006

(54) PREPARATION OF FLUORINATED ACETOPHENONES

(75) Inventors: Albrecht Marhold, Leverkusen (DE); Jens Peter Joschek, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/871,167

(22) Filed: Jun. 17, 2004

(65) Prior Publication Data

US 2005/0043559 A1      Feb. 24, 2005

(30) Foreign Application Priority Data

Jun. 16, 2003   (DE)   ................. 103 26 917

(51) Int. Cl.
*C07C 45/27*   (2006.01)
(52) U.S. Cl. ............. 568/320; 568/323; 568/335
(58) Field of Classification Search ........... 568/320, 568/323, 335
See application file for complete search history.

(56) References Cited

U.S. PATENT DOCUMENTS

| | | | |
|---|---|---|---|
| 4,405,824 A * | 9/1983 | Kobayashi et al. | ......... 570/144 |
| 5,990,357 A | 11/1999 | Zawadiak et al. | .......... 568/320 |
| 6,232,258 B1 | 5/2001 | Ishii et al. | ................. 502/155 |
| 6,355,634 B1 | 3/2002 | Isenring et al. | .......... 514/227.5 |
| 6,407,100 B1 | 6/2002 | Isenring et al. | .......... 514/227.5 |

OTHER PUBLICATIONS

Ishii, Yasutaka et al: "Alkane Oxidation with Molecular Oxygen Using a New Efficient Catalytic System: N-Hydroxyphthalimide (NHPI) Combined with Co(acac)n (n=2 or 3)" Journal of Organic Chemistry, 61(14), 4520-4526 Coden: Joceah; ISSN: 0022-3263, 1996, XP000591064 *Seite 4523, Spalte 1*.

Ishii, Yasutaka et al: Novel Catalysis by N-Hydroxyphthalimide in the Oxidation of Organic Substrates by Molecular Oxygen Journal of Organic Chemistry, 60(13), 3934-5 Coden: Joceah; ISSN: 0022-3263, 1995, XP000512054 *Tabelle 1*.

Ishii, Yasutaka et al: "A new strategy for alkane oxidation with $O_2$ using N-hydroxyphthalimide (NHPI) as a radical catalyst" Catalysis Surveys from Japan (1999) 3, pp. 37-35.

Ishii, Yasutaka et al "Innovation of Hydrocarbon Oxidation with Molecular Oxygen and Related Reactions" Adv. Synth. Catal. 2001, 343, No. 5, pp. 393-427.

* cited by examiner

*Primary Examiner*—Sikarl A. Witherspoon
(74) *Attorney, Agent, or Firm*—Michael A. Miller

(57) ABSTRACT

The invention relates to a process for preparing fluorinated acetophenones from fluorinated aryl compounds in the presence of N-hydroxyphthalimide and the use thereof.

7 Claims, No Drawings

PREPARATION OF FLUORINATED ACETOPHENONES

BACKGROUND OF THE INVENTION

1. Field of the Invention

The invention relates to a process for preparing fluorinated acetophenones from fluorinated aryl compounds in the presence of N-hydroxyphthalimides.

2. Brief Description of the Prior Art

Fluorinated acetophenones, especially 3-trifluoromethylacetophenone, are valuable intermediates for the synthesis of active agrochemical or pharmaceutical ingredients (see also EP-A 460 575).

Acylated aromatics are prepared customarily by directly acylating aromatics in the presence of Lewis acids, but may also be prepared, for example, by oxidizing alpha-hydroxyalkylaromatics or isoalkylaromatics with N-hydroxyphthalimide (see also EP-A 796 835; Y. Ishii et al., Catalysis Surveys from Japan, 1999, 3, 27–35; Y. Ishii et al., Adv. Synth. Cat., 2001, 5, 393–427). A disadvantage of the processes is that they are restricted to electron-rich aromatics and the latter method typically proceeds with little selectivity. For fluorinated and other electron-deficient aromatics, the synthesis is generally effected via the steps of nitration, reduction of the nitroaromatic to the corresponding aniline and diazotization with aldoxime to the corresponding acetophenone. A disadvantage of this process is that it proceeds over several stages and thus requires a high degree of apparatus complexity, and also that the overall yield is only moderate.

There is therefore a need to provide an efficient process for preparing fluorinated acetophenones starting from readily available reactants.

SUMMARY OF THE INVENTION

Surprisingly, a process has now been found for preparing compounds of the formula (I)

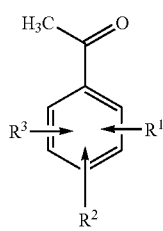

in which
$R^1$ is $C_1$–$C_{12}$-perfluoroalkyl or $C_1$–$C_{12}$-perfluoroalkoxy
$R^2$ is hydrogen, fluorine, chlorine, bromine, $C_1$–$C_4$-alkyl, $C_1$–$C_4$-alkoxy, nitro, cyano or $COOR^4$ where $R^4$ is hydrogen or $C_1$–$C_4$-alkyl and
$R^3$ is hydrogen, fluorine or chlorine, or
two of the $R^1$, $R^2$ and $R^3$ radicals together are difluoromethylenedioxy, tetrafluoroethylene-1,2-dioxy, 2-oxytetrafluoroethyl or (oxydifluoromethoxy)difluoromethyl,
which is characterized in that compounds of the formula (IIa) or (IIb)

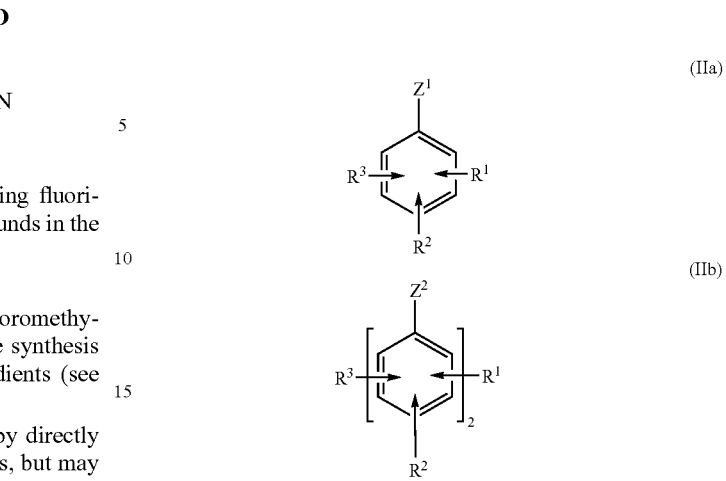

in which
$R^1$, $R^2$ and $R^3$ are each as defined above and
$Z^1$ is isopropyl, propenyl, 2-hydroxy-2-propyl, 2-hydroperoxy-2-propyl or 1-methyloxiranyl and
$Z^2$ is O,O-bis(2-oxydiisopropyl)
are converted
in the presence of 0.1 to 30 mol % of an N-hydroxyphthalimide
in the presence of an oxidizing agent.

In the context of the invention, all radical definitions, parameters and illustrations above and listed hereinbelow, specified in general or within areas of preference, i.e. the particular areas and areas of preference, may be combined as desired.

DETAILED DESCRIPTION OF THE INVENTION

Alkyl and alkoxy are in each case independently a straight-chain, cyclic, branched or unbranched alkyl and alkoxy radical respectively. The same applies to the non-aromatic moiety of an arylalkyl radical.

$C_1$–$C_4$-Alkyl is, for example, methyl, ethyl, isopropyl, n-butyl, sec-butyl and tert-butyl.

$C_1$–$C_4$-Alkoxy is, for example, methoxy, ethoxy, n-propoxy, isopropoxy, n-butoxy, sec-butoxy and tert-butoxy.

Perfluoroalkyl and perfluoroalkoxy are in each case a straight-chain, cyclic, branched or unbranched alkyl and alkoxy radical respectively, each of which are fully substituted by fluorine atoms.

For example, $C_1$–$C_{12}$-fluoroalkyl is trifluoromethyl, pentafluoroethyl, heptafluoroisopropyl, nonafluorobutyl, perfluorooctyl and perfluorododecyl.

For example, $C_1$–$C_{12}$-fluoroalkoxy is trifluoromethoxy, pentafluoroethoxy, heptafluoroisopropoxy and nonafluorobutoxy.

The preferred substitution patterns for compounds of the formulae (I) and (IIa,b) are defined hereinbelow:

$R^1$ is preferably $C_1$–$C_4$-perfluoroalkyl or $C_1$–$C_4$-perfluoroalkoxy, more preferably trifluoromethyl or trifluoromethoxy.

$R^2$ is preferably hydrogen, fluorine, chlorine, methyl, ethyl, methoxy, nitro, cyano or COOH, more preferably hydrogen, fluorine or chlorine, most preferably hydrogen or fluorine.

$R^3$ is preferably hydrogen or fluorine, more preferably hydrogen.

Preference is further given to compounds in which two of the R¹, R² and R³ radicals together are difluoromethylenedioxy or tetrafluoroethylene-1,2-dioxy.

Preferred compounds are also those which will be the formula (IIa) and in which $Z^1$ is isopropyl and propenyl, even greater preference being given to isopropyl.

Particularly preferred individual compounds of the formula (IIa) include:

3-trifluoromethylisopropylbenzene, 4-trifluoromethylisopropylbenzene, 5-isopropyl-2,2-difluorobenzodioxole, 4-chloro-3-trifluoromethylisopropylbenzene, 4-chloro-2-trifluoromethylisopropylbenzene,4-trifluoromethoxyisopropylbenzene.

Particularly preferred compounds of the formula (I) are:

3-trifluoromethylisopropylbenzene, 4-trifluoromethylisopropylbenzene and 5-isopropyl-2,2-difluorobenzodioxole.

Compounds of the formula (IIa) in which $Z^1$ is isopropyl, are preferably prepared by reacting compounds of the formula (III)

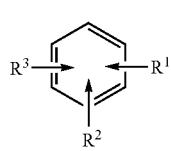

(III)

in which

R¹, R² and R³ are each as defined above with propene or isopropyl chloride, preferably with propene, in the presence of hydrogen fluoride, preferably in hydrogen fluoride.

In this reaction, various isomers may occur and may be distillatively separated, in which case the undesired isomer may advantageously be recycled into the reaction for reisomerization.

Preferred N-hydroxyphthalimides are those of the formulae (IVa) and (IVb)

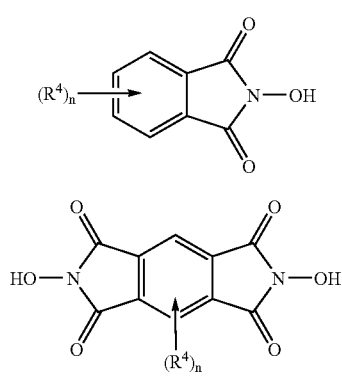

in which the R⁴ radicals are in each case independently fluorine, chlorine, bromine, trifluoromethyl, cyano or nitro, and n is zero, one, two, three or four.

Particular preference is given to N-hydroxyphthalimides of the formula (IVa), very particular preference to N-hydroxyphthalimide.

If desired, the inventive conversion of compounds of the formulae (IIa) and (IIb) to compounds of the formula (I) may also be carried out in the presence of transition metals or transition metal compounds.

Suitable transition metals or transition metal compounds are, for example, cobalt, manganese, iron, copper, rhodium, osmium, ruthenium or compounds thereof.

Preferred transition metals are cobalt, manganese, rhodium and ruthenium as a cocatalyst for N-hydroxyphthalimides.

If desired, the inventive conversion of compounds of the formulae (Ia) and (IIb) to compounds of the formula (I) may also be carried out in the presence of an organic solvent.

Preference is given to those organic solvents which are at least very substantially inert towards oxygen under the reaction conditions and can at least noticeably dissolve both the substrate and the N-hydroxyphthalimides at room temperature. In this context, "noticeably" means that solutions are obtained at reaction temperature which are at least 0.1 molar, preferably at least 0.5 molar, of the particular component.

Such solvents are, for example: acetonitrile, benzonitrile, polyglycol or fluorinated solvents, for example $N(C_2F_5)_3$, 3,5-bis(trifluoromethyl)trifluoromethoxybenzene or part- or perfluorinated alkyltetrahydrofurans.

Useful oxidizing agents may be oxygen-containing gases, especially oxygen itself, air, $N_2O$ or mixtures thereof, preference is given to oxygen.

The reaction pressure may be, for example 0.2 to 100 bar, preferably 1 to 20 bar.

The reaction temperature may be, for example, 20° C. to 160° C., preferably 40 to 120° C.

The reaction time may be, for example, 1 to 72 hours, preferably 2 to 24 hours.

The reaction mixtures may be worked up in a manner known per se, for example by distillation.

In a preferred embodiment of the process according to the invention, unconverted or part-converted reactants, just like any transition metals or transition metal compounds present and/or any organic solvent present, may be recycled back into the reaction.

The compounds of the formula (I) obtainable in accordance with the invention are especially suitable as intermediates in a process for preparing active agrochemical or pharmaceutical ingredients.

In the inventive manner, the compounds of the formula (I) are obtained in good yields starting from readily available or preparable compounds, and the recycling in individual steps allows processes which are economically and ecologically even more advantageous to be achieved.

The invention is further described by the following illustrative but non-limiting examples.

EXAMPLES

Example 1

Preparation of 3-trifluoromethylacetophenone from 3-trifluoromethylisopropylbenzene In a 500 ml flask, 2.57 g of N-hydroxyphthalimide together with 15.0 g of 3-isopropylbenzotrifluoride are dissolved in benzonitrile, and the reaction mixture is subsequently degassed. The solution is saturated with oxygen and heated to 100° C. At this temperature, the mixture is stirred for 20 hours. For workup, the mixture is added to ice, filtered through a fluted filter and washed with MTBE. The filtrate is extracted with MTBE, and the combined organic phases are washed with dil. NaOH, dried and concentrated by rotary evaporation. (MTBE=methyl tert-butyl ether) Yield/conversion by GC: 65% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing compounds of the formula (I)

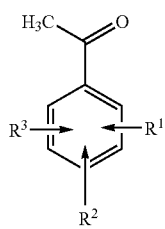

(I)

in which
R¹ is $C_1$–$C_{12}$-perfluoroalkyl or $C_1$–$C_{12}$-perfluoroalkoxy
R² is hydrogen, fluorine, chlorine, bromine, $C_1$–$C_4$-alkyl, $C_1$–$C_4$-alkoxy, nitro, cyano or COOR⁴ where R⁴ is hydrogen or $C_1$–$C_4$-alkyl and
R³ is hydrogen, fluorine or chlorine, or
two of the R¹, R² and R³ radicals together are difluoromethylenedioxy, tetrafluoroethylene-1,2-dioxy, 2-oxytetrafluoroethyl or (oxydifluoromethoxy)difluoromethyl,
comprising combining compounds of the formula (IIa) or (IIb)

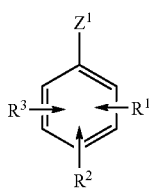

(IIa)

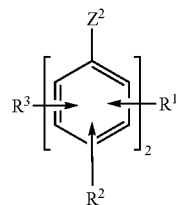

(IIb)

in which
R¹, R² and R³ are each as defined above and
Z¹ is isopropyl, propenyl, 2-hydroxy-2-propyl, 2-hydroperoxy-2-propyl or 1-methyloxiranyl and
Z² is O,O-bis(2-oxydiisopropyl)
with 0.1 to 30 mol % of an N-hydroxyphthalimide to form a mixture;
degassing the mixture; and
adding an oxidizing agent.

2. The process according to claim 1, wherein compounds of the formula (IIa) are used in which Z¹ is isopropyl and propenyl.

3. The process of claim 1, wherein compounds of the formula (IIa) are used in which Z¹ is isopropyl.

4. The process according to claim 3, wherein the compounds used are obtained by reacting compounds of the formula (III)

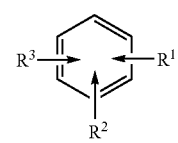

(III)

in which
R¹, R² and R³ are each as defined in claim 1 with propene or isopropyl chloride in the presence of hydrogen fluoride.

5. The process of claim 1, wherein conversion of compounds of the formulae (IIa) and (IIb) to compounds of the formula (I) is also carried out in the presence of transition metals or transition metal compounds.

6. The process claim 1, wherein the oxidizing agent used is an oxygen-containing gas.

7. The process claim 1, whereing unconverted or partially converted reactants, are recycled back into the reaction.

* * * * *